of Antibody Secreting Cells In Vitro. J of Immuno Methods 79(2)195–204, 1985.*

(12) United States Patent
Qian

(10) Patent No.: US 6,869,771 B1
(45) Date of Patent: Mar. 22, 2005

(54) METHOD FOR DISTRIBUTING EQUAL VOLUMES OF ATTACHED CONFLUENT LIVING CELLS

(75) Inventor: Yong Qian, San Diego, CA (US)

(73) Assignee: Access Business Group International LLC, Ada, MI (US)

( * ) Notice: Subject to any disclaimer, the term of this patent is extended or adjusted under 35 U.S.C. 154(b) by 220 days.

(21) Appl. No.: 10/223,233

(22) Filed: Aug. 19, 2002

Related U.S. Application Data

(63) Continuation-in-part of application No. 09/747,791, filed on Dec. 22, 2000, now abandoned.
(60) Provisional application No. 60/171,366, filed on Dec. 22, 1999.

(51) Int. Cl.[7] .................................................. C12Q 1/24
(52) U.S. Cl. ......................... 435/30; 435/29; 435/380; 435/383
(58) Field of Search ........................... 435/29, 30, 380, 435/383, 288.4

(56) References Cited

U.S. PATENT DOCUMENTS

| 5,753,229 A | * | 5/1998 | Mordoh et al. | .......... 424/155.1 |
| 6,723,699 B1 | * | 4/2004 | Lewis et al. | .................. 514/12 |

OTHER PUBLICATIONS

Moller S. A Filter Immuno Plaque Assay for the Detection of Antibody Secreting Cells In Vitro. J of Immuno Methods 79(2)195–204, 1985.*

Forsyth E. Proliferation and Extracellular Matrix Production by Human Infragenicular Smooth Muscle Cells in Response to Interleukin–1beta. J of Vascular Surgery 26(6)1002–8, Dec. 1997.*

* cited by examiner

*Primary Examiner*—Ralph Gitomer
(74) *Attorney, Agent, or Firm*—Alticor Inc.

(57) ABSTRACT

A method for distributing an equal volume of attached confluent living cells in each well of a multi-well plate used in a bioassay, comprising the following steps:
(a) growing attached living cells on a medium until the cells are confluent; (b) treating the attached confluent living cells with an enzyme solution, whereby the solution and the attached confluent living cells make a cell suspension; (c) filtering the cell suspension with a filter; (d) collecting a cell suspension filtrate containing uniformly distributed attached confluent living cells therein; and (e) distributing an equal volume of the cell suspension filtrate into wells of a plate whereby each well has an equal volume of cells for use in any bioassay.

7 Claims, 3 Drawing Sheets

METHOD FOR DISTRIBUTING EQUAL VOLUMES OF ATTACHED CONFLUENT LIVING CELLS

This application is a continuation-in-part of U.S. patent Ser. No. 09/747,791 filed on Dec. 22, 2000 now ABN which claims the benefit under 35 U.S.C. §120 of a provisional U.S. patent Ser. No. 60/171,366 filed on Dec. 22, 1999, all of which are incorporated herein by reference.

FIELD OF THE INVENTION

The present invention relates to a method for distributing attached confluent living cells in high throughput screening bioassays. In particular, this invention relates to an in vitro method for distributing equal volumes of attached confluent living cells in individual wells of a multi-well plate used to study any attached cell based cellular and/or molecular event.

BACKGROUND OF THE INVENTION

Subcultured cells are frequently used in biological experiments to understand the nature of a particular substance such as a protein or a chemical. When a substance is tested on cells that are subcultured in wells of a multi-well plate, it is important to obtain reproducible and repeatable test results to be able to confidently rely on those results. In the past, methods of distributing cells for biological experiments provided random and unequal volumes of cells in each well of a multi-well plate that was used for testing. The unequal volume of cells created large variations in results when an equal amount of a substance was tested on the cells in each well. Therefore, scientists had to frequently perform several tests to obtain a result that was duplicated a sufficient number of times to be considered reliable.

Distributing equal volumes of attached confluent living cells in each well of a multi-well plate, including 4, 8, 12, 24, 48, 96, 384 or more well plates, has been a long-standing problem in high throughput screening bioassays partly because the trypsinization process does not guarantee equal volumes of cells in each small confluent cell group. During the trypsinization process, the enzyme trypsin reacts to the surface of attached confluent cells and gradually separates a cell or cells on the edge or surface of very large confluent cell groups. As a result, the cell suspension consists of varying sizes of confluent cell groups including single cells, small cell clusters, large cell clusters and huge cell clumps. Raising the amount of trypsin or prolonging the treatment of trypsin does not cure the separation problem because cells in the middle of a confluent cell group may never be trypsinized at all and an over-treatment with the trypsin enzyme may kill the cells that are separated early in the trypsinization process.

Adding to the difficulty in distributing an equal volume of cells in each well of a multi-well plate is the non-uniformly distributed groups of cells in the cell suspension. As such, distributing an equal volume of the cell suspension in each well of a multi-well plate does not guarantee that equal volumes of cells are present in each volume of the cell suspension. Although very large confluent cell groups are sometimes artificially picked out to avoid clogging pipette tips, the distribution of a non-uniform cell suspension to each well of a multi-well plate unavoidably and directly causes a large variation in the volume of cells in each well of a multi-well plate. Because past attached cell-based biological testing resulted in a large standard deviation, the reliability, repeatability and reproducibility of the results were questionable. Accordingly, there remains a need to obtain a uniform distribution of cells in a cell suspension as well as a need to distribute equal volumes of attached confluent living cells in individual wells of a multi-well plate to reduce the standard deviation and to improve the reproducibility, repeatability and reliability of biological test results.

SUMMARY OF THE INVENTION

Figure 1:
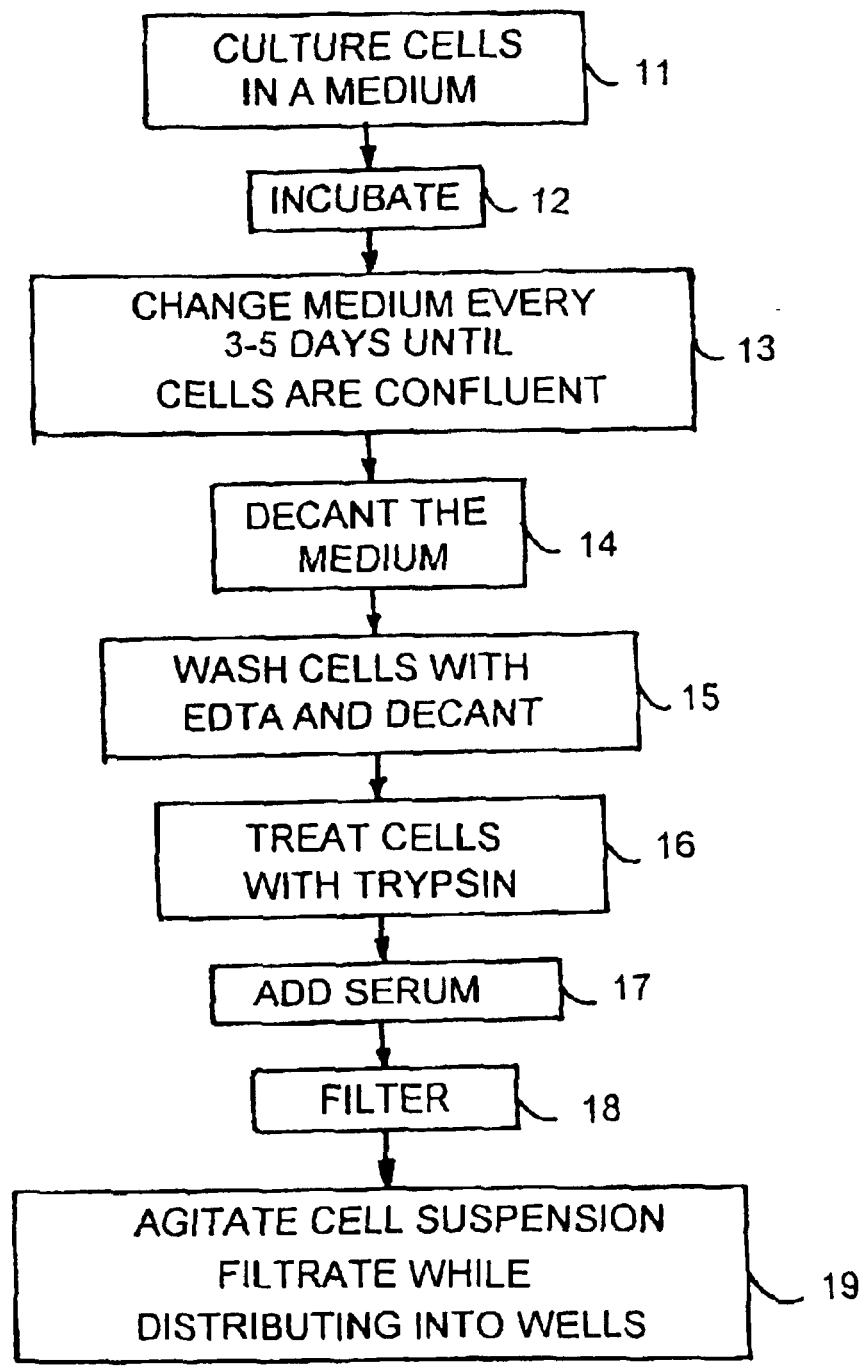
FIG. 1 is a schematic illustration of the steps in accordance with the preferred embodiment of the present invention.

The foregoing problems are solved by providing a method of distributing equal volumes of attached confluent living cells in each well of a multi-well plate including the following steps: (1) growing attached living cells on a medium until the cells are confluent; (2) treating the attached confluent living cells with an enzyme solution, whereby the attached confluent living cells and the enzyme solution make a cell suspension; (3) filtering the cell suspension with a filter having a pore size that is smaller than at least one of the clusters of cells in the cell suspension; (4) collecting a cell suspension filtrate; and (5) distributing an equal volume of the cell suspension filtrate into individual wells of a multi-well plate for use in any bioassay.

The use of a filter to screen out clusters of cell groups provides a uniform distribution of cells and cell groups in the cell suspension filtrate. This uniformity allows one to calculate the number of cells in each measured volume of the cell suspension and, thus, enables one to distribute equal volumes of cells in each well of a multi-well plate for use in a bioassay.

These and other objects, advantages, and features of the invention will be better understood by reference to the drawings and the detailed description of the preferred embodiment.

DETAILED DESCRIPTION OF THE PREFERRED EMBODIMENT

"Attached confluent living cells" is a term used in relation to animal cell/tissue cultures to describe the growth and morphological behavior of cells when they are cultured in vitro. Attached confluent living cells are those that attach to each other and the container that they are cultured in, such as a petri dish. Proteins and lipoproteins in cells create the attachment between cells.

The term "high throughput screening" is a screening assay which is performed to test tens of or hundreds of samples simultaneously. For example, using a 16, 24, 48, 96, or 384 well plate to do a bioassay to test multiple samples simultaneously is considered "high throughput screening."

One embodiment of the present invention includes: (1) growing attached living cells on a medium until the cells are confluent; (2) treating the attached confluent living cells with an enzyme solution, whereby the solution and the attached confluent living cells make a cell suspension; and (3) filtering the cell suspension with a filter having a pore size that is smaller than at least one of the clusters of cells in the cell suspension; and (4) collecting a cell suspension filtrate containing uniformly distributed attached confluent living cells therein; (5) obtaining a sample of the cell suspension filtrate; (6) performing serial dilutions of the sample to enable counting the number of cells under a microscope; (7) counting the number of cells under a microscope and multiplying the number of cells by a dilution factor which corresponds with the serial dilutions such that the number of cells in a predetermined volume of the cell suspension filtrate is calculable; and (8) distributing an equal volume of the cell suspension filtrate into wells for use in any bioassay. The cell suspension filtrate can be directly distributed in desired volumes into each well of a multi-well plate without performing the intermediate steps of 5–7.

Figure 2:
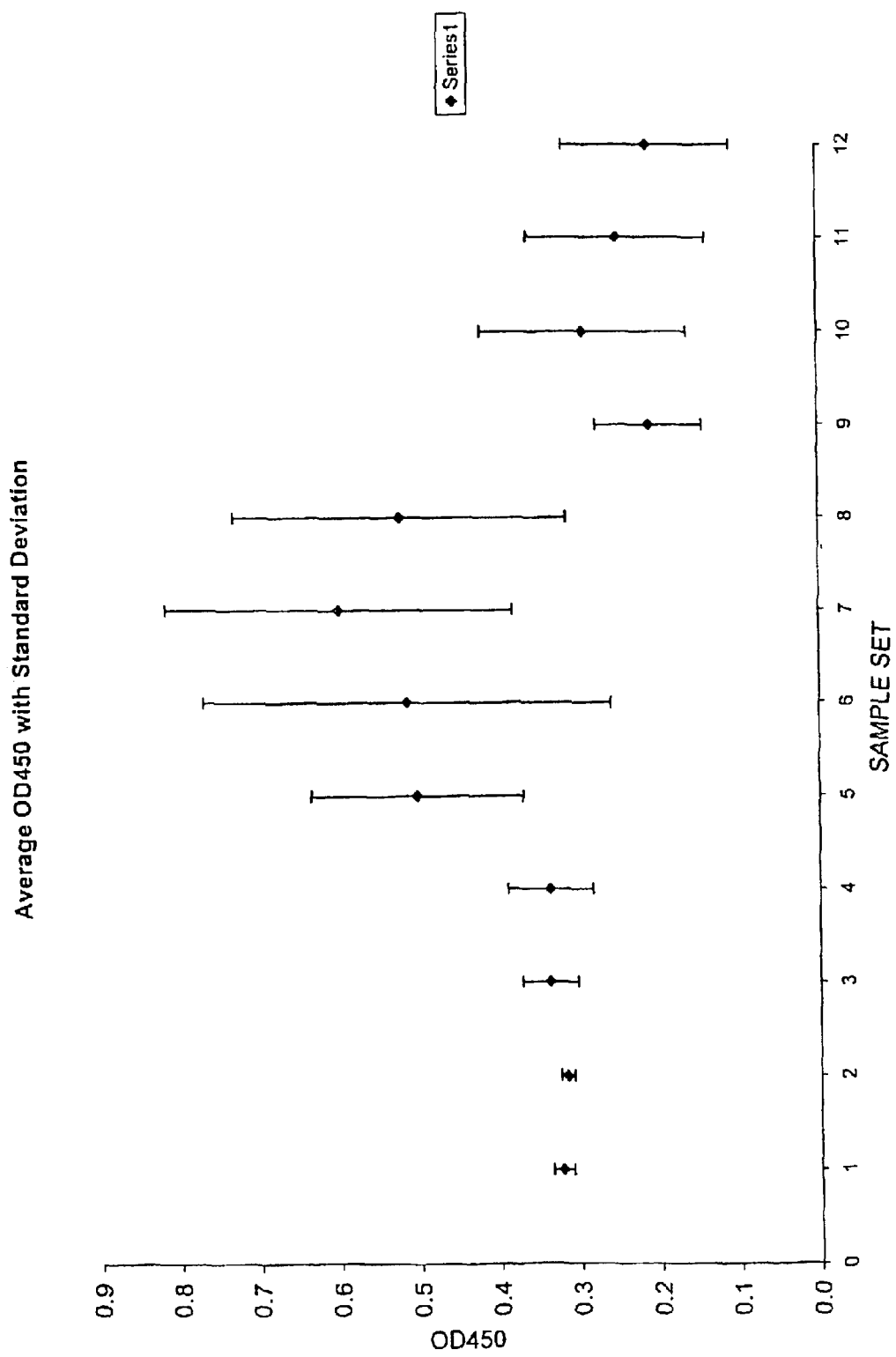
FIG. 2 is a graph displaying the optical density range for each of the 12 sample sets from a 96-well plate; each sample set contained data from readings of 8 samples in 8 corresponding wells.

FIG. 1 illustrates a preferred embodiment of the present invention. Cells are grown on a medium in a tissue culture container 11. It is preferred that alpha minimum essential medium is used ("alpha-MEM") in conjunction with calf serum. Antibiotics can be added to the medium to help insure sterile conditions. It is preferable to place the container with the cells in a tissue culture incubator 12 set at 37° C. having 5–6% carbon dioxide and 98% humidity. After 16 to 20 hours, cells attach to the bottom of the tissue culture container. Fresh medium is changed every 3 to 5 days until cells are confluent 13. For optimal cell growth, different cell lines may require different growth conditions which may include varying the medium, the serum, the antibiotic, and the carbon dioxide parameters. Additionally, the cell culture container may differ in size, volume and texture according to the experimental plan. It is preferable to keep the container closed. It is also preferable to keep the container under sterile conditions to avoid contamination, even though antibiotics may have been added to the medium. This enables everything to remain sterile during the operating procedures, including opening the container to change the medium or to treat the cells with trypsin. In FIG. 2, all steps, except steps 11 and 12 are performed under sterile conditions. Any cell line from any organism including, but not limited to, animal cells which attach together after division or growth may utilize this procedure.

Next, it is preferred that the medium be decanted to prevent the serum or other agents from inhibiting the action of the trypsin enzyme 14. Then, it is preferred that the cells are washed with EDTA and decanted 15. The cells are now ready to be treated with trypsin 16. The amount of trypsin used in the trypsinization process depends on the size of the cell culture container, the amount of attached cells to be treated, and the time of the treatment. Subjecting the container having the trypsin enzyme to a temperature of 37° C. will facilitate the separation of the cells from each other and from the container. After incubating for about 5 to 10 minutes, the container can be gently shaken to determine whether the suspension is cloudy. When cells are separated from the container, the suspension becomes cloudy and sheets of cells may come off the container. If cells do not come off the container, more trypsin may be added or treated up to 30 minutes or both. If after 30 minutes, only a portion of the cells separate from the container, a sterile scraper may be used to remove the majority of the cells. It is preferable to add serum to the cell suspension in a volume that is equal to the volume of the enzyme solution 17. The serum stops the enzymatic reaction of trypsin. The serum also serves as a buffer to suspend cells and to minimize the physical damage of cells in the following filtration step. Other trypsin inhibitors may be used in this step in conjunction with the serum.

The cell suspension is next filtered preferably using a sterile filter of any desired pore size to remove undesirable clusters of cells while allowing desirable cell clusters to pass through to form the cell suspension filtrate 18. To determine the desired pore size, the following formula may be used: $F = M \times N \times C$. F is the filter pore size desired for the present method. M is the mean cell diameter of the individual cells in the attached confluent living cell cluster. For human liver cells, a single cell may measure about 6 $\mu$m to 8 $\mu$m. N is the number of cells in the majority of the cell clusters in the cell suspension filtrate. For example, in the case of human liver cells, over 50% of the cell clusters in the cell suspension filtrate may contain 6 cells so N would equal 6. C is the correction coefficient to further adjust the pore size to avoid jamming the pores of the filter and damaging cells. For human liver cells, C is desirable over 3. Those of ordinary skill in the art will appreciate that the value of C will also depend on the density of the cell population in the suspension. The more dense the cell population, the larger the correction coefficient. The pore size of the filter may range from 50 $\mu$m to 500 $\mu$m depending on the cell size and the cell line property. The pore size may range from about 100 $\mu$m to about 300 $\mu$m for human liver cells, most preferably, about 150 $\mu$m. If the majority of the cell clusters are human liver cells having 6 cells per cluster, then an example may be as follows: M=7, N=6, and C=3.5 (7 $\mu$m×6×3.5=147 $\mu$m). To avoid mechanical damage to cells and/or passage of undesirable cell clusters, it is preferable to allow the suspension to pass through the filter by means of gravity rather than applying artificial force.

The uniformly distributed cell suspension filtrate is sampled and diluted in order to count the number of cells in the sample under a microscope. For example, O. 1 ml of a 10 ml of the cell suspension filtrate may be sampled and diluted with a serial dilution in any format (e.g. $2^2$, $2^3$, ... $2^{12}$). Dilution should be repeated so that one can obtain a clear cell count from the sample by using a microscope. The concentration of cells in the cell suspension filtrate can then be calculated according to dilution factors. Next, the cell suspension filtrate is diluted to the desired concentration with the appropriate culture medium. The desired volume of cell suspension filtrate having the desired volume of cells is finally distributed in each well of multi-well plates 19. While distributing, it is preferable to shake the container having the cell suspension filtrate to maintain the uniformity of the cell distribution. Cells will attach in 16 to 20 hours. The medium can be changed with any treatments or used for any purpose.

The following example illustrates, but does not limit, the present invention.

EXAMPLE

The following attached-cell based essay in 96-well plate was conducted to quantify protein in each well and to show the reduced standard deviation using the method of present invention versus conventional subculturing methods. Cells (Rat liver clone 9 obtained from American Type Culture Collection, Rockville, Md.) were grown according to manufacturer's instruction and subcultured in 100 ml culture medium. The culture medium contained 89 ml alpha-MEM and 10 ml calf serum (both provided by GIBCO, Rockville, Md.) and 1 ml (100×) antibiotic-antimytoic containing 10,000 units streptomycin sulfate, 10,000 units penicillin G sodium and 25 $\mu$g amphotericin (supplied by Sigma, St. Louis, Mo.). The cells were subcultured in a 150×25 mm polystyrene tissue culture dish (supplied by Becton Dickinson and Company, Franklin Lakes, N.J.). The culture dish was placed in an incubator (supplied by Revco, Asheville, N.C.) with the following conditions: 6% carbon dioxide, 98% humidity and 37° C. The medium was decanted and the cells were washed with EDTA and subsequently treated with 5 ml trypsin-EDTA (1×) (supplied by Sigma) for 5 to 15 min at 37° C. until the suspension became cloudy. Then, 5 ml of serum was added to the suspension. A coarse filter was used to filter out large clusters of attached cells from the cell suspension. The cell density of the suspension filtrate was examined under a microscope and counted at $2^8$ to $2^{12}$ dilution. Thus, the cell density of the suspension filtrate is calculated and properly diluted with the cell culture medium. The 96-well tissue culture plate was a Microtest™ 96 with a flat bottom and a low evaporation lid (supplied by Becton Dickinson and Company, Franklin Lakes, N.J.).

Wells in sample sets 1 and 2 were seeded with about 100 μl (about 3,000 cells) of the cell suspension filtrate that was subject to the steps of the present invention. Wells in sample sets 3 and 4 were seeded with the same volume of cell suspension as sample sets 1 and 2 but without stirring the mix. Wells in sample sets 5 to 8 were seeded with the same volume of cell suspension, which was not subject to the methods of the present invention. Wells in sample sets 9 to 12 were seeded with half of the volume of cell suspension that was not subject to the methods of the present invention. The final total cell culture medium in each well was adjusted to the total volume of 200 μl. After one day, cells began attaching to the bottom of each well. The medium was changed and cultured for another 24 hours and assayed for protein content using a bicinchoninic acid ("BCA") protein assay kit (supplied by Sigma). The medium in each well was shaken off, washed with tap water, and blotted. 30 μl of 0.3% digitonin was added to each well of the 96-well plate and treated at 37° C. for 10 min to lyse cells. Then the plate was shaken at room temperature for 5 min. For the protein assay, 200 μl of a reaction solution containing 49 parts of a BCA and 1 part of 4% cupric sulfate pentahydrate was added to the wells of the standard or samples. Plates were put in 37° C. for 30 min and were read at an optical density of 560 ($OD_{560}$) using a Vmax kinetic microplate reader (obtained from Molecular Devices, Sunnyvale, Calif.).

Figure 3:
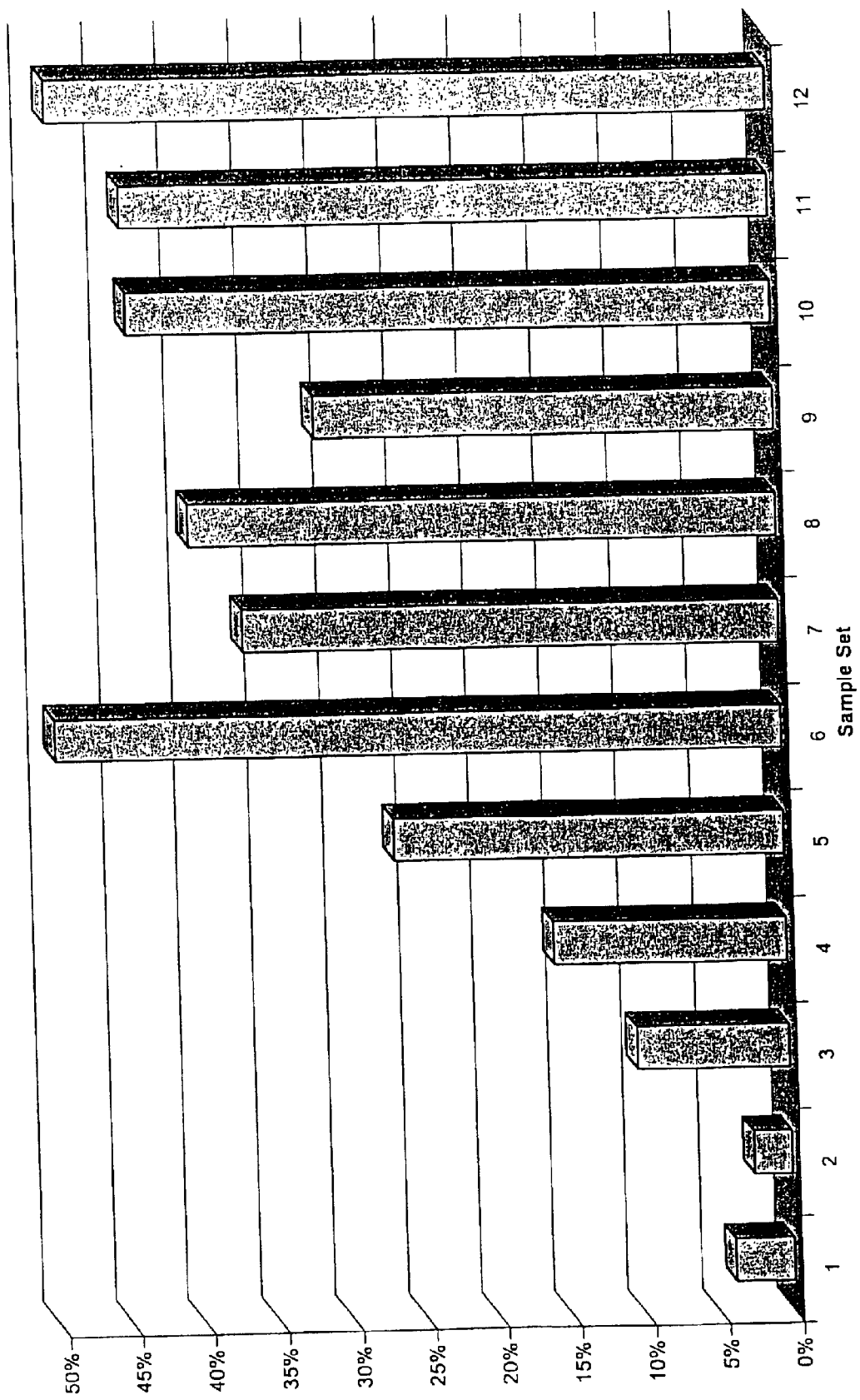
FIG. 3 is a bar graph corresponding with the graph of FIG. 2 and depicting the standard deviation for each sample set.

The results as shown in Table I and FIG. 3 and FIG. 4 demonstrate that the cells that were not subject to the methods of the present invention (sample sets 5–12) have a larger standard deviation than the cells that were subject to the methods of the present invention (sample sets 1–4). Thus, the present invention reduces the standard deviation of the cells in each well and improves the reproducibility, repeatability, and reliability of bioassay results than that by using the conventional subculturing methods.

TABLE 1

Optical Density for Each of the 96 Wells

| Set | Sample | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| | 0.341 | 0.317 | 0.366 | 0.387 | 0.404 | 0.272 | 0.629 | 0.479 | 0.171 | 0.195 | 0.195 | 0.204 |
| | 0.323 | 0.332 | 0.314 | 0.323 | 0.536 | 0.72 | 0.65 | 0.391 | 0.178 | 0.425 | 0.125 | 0.21 |
| | 0.34 | 0.316 | 0.361 | 0.373 | 0.551 | 0.375 | 0.411 | 0.708 | 0.325 | 0.171 | 0.179 | 0.198 |
| | 0.321 | 0.304 | 0.345 | 0.263 | 0.325 | 1.022 | 0.933 | 0.755 | 0.151 | 0.41 | 0.344 | 0.161 |
| | 0.318 | 0.316 | 0.263 | 0.341 | 0.721 | 0.42 | 0.821 | 0.705 | 0.305 | 0.171 | 0.382 | 0.453 |
| | 0.311 | 0.317 | 0.364 | 0.38 | 0.438 | 0.603 | 0.326 | 0.183 | 0.182 | 0.304 | 0.175 | 0.144 |
| | 0.31 | 0.316 | 0.332 | 0.258 | 0.633 | 0.315 | 0.651 | 0.619 | 0.185 | 0.47 | 0.407 | 0.114 |
| | 0.309 | 0.308 | 0.347 | 0.38 | 0.403 | 0.382 | 0.364 | 0.329 | 0.187 | 0.183 | 0.185 | 0.205 |
| Average (Avg.) | 0.322 | 0.316 | 0.337 | 0.336 | 0.501 | 0.514 | 0.598 | 0.521 | 0.211 | 0.291 | 0.249 | 0.211 |
| Standard Deviation (SD) | 0.013 | 0.008 | 0.035 | 0.053 | 0.133 | 0.254 | 0.218 | 0.208 | 0.066 | 0.128 | 0.110 | 0.104 |
| SD/Avg. | 0.040 | 0.026 | 0.103 | 0.157 | 0.265 | 0.495 | 0.364 | 0.399 | 0.312 | 0.438 | 0.441 | 0.491 |

The present invention may be used for any attached cell based testing including, but not limited to, gene up regulation or enzyme induction, for example, the induction of quinone reductase and other phase II enzymes; gene down regulation or enzyme inhibition, for example, the inhibition of cyclooxygenases, cGMP or cAMP phosphodiesterases, lipoxygenases, lipases, proteases, caspase, DNA polymerases, helicases by a compound or a group of compounds; attached cell based cell signalling (apoptosis etc); and receptor binding, for example, GABA A receptor binding, estrogen receptor binding, cGMP/cAMP receptor binding, and prostaglandin receptor binding.

These attached cell based tests may be also used for high throughput screening for drug or natural product development for functions of detoxification, energy enhancement, anti-inflammation, relationship enhancement, weight control, weight loss, anti-cancer, anti-aging, anti-HIV, anti-diabetes etc.

It is to be understood that the foregoing specification of this invention is illustrative and has been described in relation to certain preferred embodiments. It will be apparent to those skilled in the art that the invention is susceptible to alteration and that certain other details described herein can very considerably without departing from the basic principles of the invention as defined in the following claims.

What is claimed:

1. A method of distributing equal number of attached confluent living cells in individual wells of a multi-well plate comprising:
    (a) growing attached living cells on a medium until the cells are confluent;
    (b) treating the attached confluent living cells with an enzyme solution, whereby the solution and the attached confluent living cells make a cell suspension;
    (c) filtering the cell suspension with a filter having a pore size that is about 150 μm to remove attached confluent living cells having a diameter greater than about 150 μm, whereby the cell suspension filtrate contains substantially uniformly distributed attached confluent living cells having a diameter less than about 150 μm; and
    (d) distributing an equal volume of the cell suspension filtrate into wells of a plate; whereby each well has substantially equal number of cells for use in any bioassay.

2. The method of claim 1 further comprising the following steps between steps (c) and (d):
(a) obtaining a sample of the cell suspension filtrate;
(b) performing serial dilutions of the sample to enable counting the number of cells under a microscope;
(c) counting the number of cells under a microscope and multiplying the number of cells by a dilution factor which corresponds with the serial dilutions such that the number of cells in a predetermined volume of cell suspension filtrate may be calculated; and
(d) distributing an equal volume of the cell suspension filtrate into wells of a plate; whereby each well has substantially equal number of cells for use in any bioassay.

3. The method of claim 1 wherein the medium includes about 89 ml to about 89.5 ml of alpha-MEM, about 10 ml of calf serum, and about 0.5 ml to about 1 ml triantibiotic.

4. The method of claim 1 wherein the treating step comprises treating the attached confluent living cells for about 5 minutes to about 15 minutes at 37° C. with about 5 ml of trypsin-EDTA and subsequently neutralizing the trypsin with about 5 ml of a trypsin inhibitor.

5. The method of claim 2 wherein the serial dilutions performed in step (b) is about $2^8$ to about $2^{12}$.

6. A method of distributing an equal number of attached confluent living cells in individual wells of a multi-well plate comprising:
(a) disaggregating attached confluent living cells;
(b) filtering the attached confluent living cells with a filter having a pore size according to the formula: $F = M \times N \times C$, where F is the filter pore size, M is a mean cell diameter of the individual cells in an attached confluent living cell cluster, N is the number of cells in a majority of the cell clusters in a cell suspension filtrate, and C is a correction coefficient of pore size, to remove attached confluent living cells having a diameter greater than about 150 μm, whereby the cell suspension filtrate contains substantially uniformly distributed attached confluent living cells having a diameter less than about 150 μm;
(c) diluting the filtrate; and
(d) distributing an equal volume of the cell suspension filtrate to individual wells of a multi well plate;
whereby individual wells have substantially equal number of cells for use in any bioassay.

7. A method of distributing an equal number of attached confluent living cells in individual wells of a multi-well plate comprising:
(a) growing attached living cells on a medium until the cells are confluent;
(b) decanting the medium;
(c) washing the attached confluent living cells with EDTA;
(d) treating the attached confluent living cells for about 5 minutes to about 15 minutes at 37° C. with about 5 ml of trypsin-EDTA;
(e) neutralizing the trypsin with about 5 ml of calf serum, whereby the trypsin-EDTA, the serum, and the attached confluent living cells make a cell suspension;
(f) filtering the cell suspension with a filter having a pore size that is about 150 μm to remove attached confluent living cells having a diameter greater than about 150 μm, whereby the cell suspension filtrate contains substantially uniformly distributed attached confluent living cells having a diameter less than about 150 μm;
(h) collecting a cell suspension filtrate containing uniformly distributed attached confluent living cells therein:
(h) obtaining a sample of the cell suspension filtrate;
(i) performing a serial dilutions of the sample to enable counting the number of cells under a microscope;
(j) counting the number of cells under a microscope and multiplying the number of cells by a dilution factor which corresponds with the serial dilutions such that the number of cells in a predetermined volume of cell suspension filtrate may be calculated; and
(k) distributing an equal volume of the cell suspension filtrate into wells of a plate; whereby each well has an equal number of cells for use in any bioassay.

* * * * *